(12) United States Patent
Vertesy et al.

(10) Patent No.: US 7,148,254 B2
(45) Date of Patent: Dec. 12, 2006

(54) 2-PHENYLBENZOFURAN DERIVATIVES, A PROCESS FOR PREPARING THEM, AND THEIR USE

(75) Inventors: Laszlo Vertesy, Eppstein-Vockenhausen (DE); Michael Kurz, Hofheim (DE); Astrid Markus-Erb, Liederbach (DE); Luigi Toti, Hochheim (DE)

(73) Assignee: Sanofi-Aventis Deutschland GmbH, Frankfurt (DE)

( * ) Notice: Subject to any disclaimer, the term of this patent is extended or adjusted under 35 U.S.C. 154(b) by 124 days.

(21) Appl. No.: 10/972,546

(22) Filed: Oct. 25, 2004

(65) Prior Publication Data

US 2005/0137254 A1     Jun. 23, 2005

Related U.S. Application Data

(60) Provisional application No. 60/552,685, filed on Mar. 12, 2004.

(30) Foreign Application Priority Data

Oct. 31, 2003   (DE) ................. 103 51 315

(51) Int. Cl.
   A61K 31/34   (2006.01)
   C07D 307/86  (2006.01)
   C12P 17/04   (2006.01)
   C12N 1/18    (2006.01)

(52) U.S. Cl. .............. 514/469; 549/469; 435/126; 435/256.1

(58) Field of Classification Search ........... 549/469; 514/469
   See application file for complete search history.

(56) References Cited

U.S. PATENT DOCUMENTS 6,043,071 A   3/2000   DeBouck et al.

FOREIGN PATENT DOCUMENTS

| | | |
|---|---|---|
| GB | 2386891 A | 10/2003 |
| JP | 2001-286292 | 10/2001 |
| WO | WO 02/10156 A1 | 2/2002 |
| WO | WO 03/097815 A2 | 11/2003 |

OTHER PUBLICATIONS

Barrow et al, Sprioquinazoline, A Novel Substance P Inhibitor With A New Carbon Skeleton, Isolated From *Aspergillus flavipes*, Journal of Natural Products, vol. 57, No. 4, 1994, pp. 471-476.

Brock et al, Microbial Genetics, Biology of Microorganisms, 7th Edition, Chapter 7, pp 238-247.

Kohno et al, TMC-169, a New Antibiotic of the Aspochalasin Group Produced by *Aspergillus flavipes*, Journal of Antibiotics, vol. 52, No. 6, 1999, pp. 575-577.

March J., Advanced Organic Chemistry, Reactions, Mechanisms, and Structure, Advanced Organic Chemistry, John Wiley & Sons, 4th Edition, 1992.

Raistrick et al, Flavipin, a Crystalline Metabolite of *Aspergillus flavipes*, Biochem J., Vold. 63, 1956, pp. 395-406.

Raistrick et al, Studies in the Biochemistry of Micro-organisms; Flavipin, A Crystalline Metabolite Of *Aspergillus flavipes*, Dept. of Biochem, London School of Hygiene and Tropical Medicine, Univ. of London, 1956, pp. 395-406.

Ravin, L. J., Preformulation, Remington's Pharmaceutical Sciences, 17, 1985, pp. 1409-1423.

Stolp H., Microbial ecology: organisms, habitata, activities, Cambridge University Press, Cambridge, GB, 1988, p. 180.

Sulzenbacher et al, Crystal Structure of *Streptococcus pneumoniae* N-Acetyl-glucosamine-1-phosphate Uridyltransferase Bound to Acetyl-coenzyme A Reveals a Novel Active Site Architecture, Journal of Biological Chemistry; vol. 276, No. 15, 2001, 11844-11851.

*Primary Examiner*—Bernard Dentz
(74) *Attorney, Agent, or Firm*—Irving Newman

(57) ABSTRACT

The present invention relates to 2-phenylbenzofurans of formula (I)

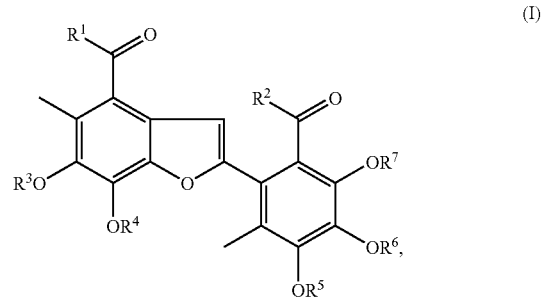

which are formed, during fermentation, by the microorganism Aspergillus flavipes ST003878 (DSM 15290), to a process for preparing them and to their use as pharmaceuticals for the treatment and/or prophylaxis of bacterial infectious diseases or mycoses.

10 Claims, No Drawings

2-PHENYLBENZOFURAN DERIVATIVES, A PROCESS FOR PREPARING THEM, AND THEIR USE

CROSS-REFERENCE TO RELATED APPLICATIONS

This application claims the benefit of priority of German Patent Application No. 10351315.9-44 filed Oct. 31, 2003, as well as the benefit of U.S. Provisional Application No. 60/552,685, filed Mar. 12, 2004.

FIELD OF THE INVENTION

The present invention relates to 2-phenylbenzofurans of formula (I)

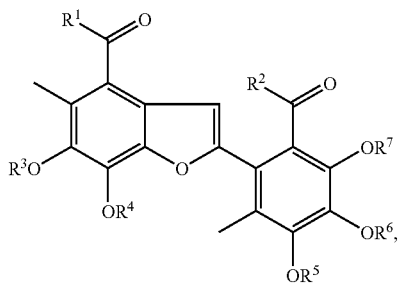

which are formed, during fermentation, by the microorganism Aspergillus flavipes ST003878 (DSM 15290), to a process for preparing them and to their use as pharmaceuticals for the treatment and/or prophylaxis of bacterial infectious diseases or mycoses.

BACKGROUND OF THE INVENTION

A large number of antibiotics are employed therapeutically for treating infectious diseases caused by bacteria. However, the pathogens are becoming increasingly resistant to the drugs employed. Indeed, there is even the threat of serious danger arising due to what are termed multiresistant organisms, which have not merely become resistant to single antibiotic groups, such as β-lactam antibiotics, glycopeptides or macrolides, but in fact carry several resistances simultaneously. There even exist pathogens which have become resistant to all the antibiotics which are commercially available. It is no longer possible to treat infectious diseases which are caused by these organisms. For this reason, there is a great need for new compositions which can be used against resistant organisms While many thousands of antibiotics have been described in the literature, most of them are too toxic to be used as drugs.

The cell walls of Gram-positive and Gram-negative bacteria consist, for the most part, of peptidoglycan (murein), which, as what is termed the murein sacculus, encloses the cell completely and lends it mechanical stability as well as helping to determine its morphological form. Peptidoglycan is a macromolecule which is composed of an alternating sequence of the 1,4-β-glycosidically linked amino sugars, N-acetylglucosamine and N-acetylmuramic acid. Crosslinkings by way of short peptide bridges provide the sugar chains with a high degree of stability. The biosynthesis of peptidoglycan is catalyzed by a number of enzymes which are either dissolved in cytoplasm or else membrane-bound. Many of these enzymes are specific to bacteria, and represent ideal points of attack in the search for new antibiotics.

The bifunctional bacterial N-acetylglucosamine-1-phosphate uridyltransferase (GlmU) catalyzes the formation of UDP-N-acetylglucosamine from glucosamine-1-phosphate in a two-step reaction. UDP-N-acetylglucosamine is a fundamental building block in bacterial cell wall biosynthesis; accordingly, inhibiting its formation is therefore a promising route for finding novel antibacterial therapeutic agents (Sulzenbacher et al., J. Biol. Chem. 2001, 276 (15), 11844–11851).

There have already been reports of compounds from cultures of Aspergillus flavipes, such as flavipin (Raistrick et al., Biochem. J. 1956, 63, 395), which has been described as being an inhibitor of the respiratory chain, and the phytotoxin flavipucine (Findlay et al., J. C. S. Perkin I 1972, 2071) as well as the compound F-90558 (Kuraya et al., JP 20012862292 A2), which have been described as being antineoplastic agents. Pyrimidin-2-ylamine-substituted phenylbenzofurans are described, for example, in Burri et al., WO 02/10156.

SUMMARY OF THE INVENTION

It has now been found, surprisingly, that the strain Aspergillus flavipes ST003878 (DSM 15290) is able to form novel antibiotics which are effective inhibitors of GlmU and are suitable for use as model structures for developing additional agents possessing antibacterial activity.

The invention relates to a compound of formula (I)

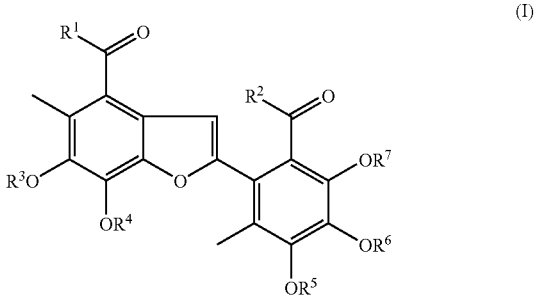

where
$R^1$ and $R^2$ are, independently of each other, H, OH or —O—($C_1$–$C_6$)-alkyl, and
$R^3$, $R^4$, $R^5$, $R^6$ and $R^7$ are, independently of each other, H, —($C_1$–$C_6$)—alkyl or —C(O)—($C_1$–$C_6$)-alkyl,
or a physiologically tolerated salt of a compound of formula (I).

($C_1$–$C_6$)-Alkyl denotes a straight chain or branched hydrocarbon group having 6 carbon atoms, for example, methyl (Me), ethyl, n-propyl, isopropyl, tert-butyl or n-hexyl, preferably methyl.

Preference is given to $R^1$ and $R^2$ in the compound of formula (I) being H.

Preference is furthermore given to $R^3$, $R^4$, $R^5$, $R^6$ and $R^7$ in the compound of formula (I) being, independently of each other, H or methyl.

Particular preference is given to $R^1$ and $R^2$ in the compound of formula (I) being H and to $R^3$, $R^4$, $R^5$, $R^6$ and $R^7$ being, independently of each other, H or methyl.

In addition, the invention relates to a compound of the formula (I) which is characterized by a compound of formula (II)

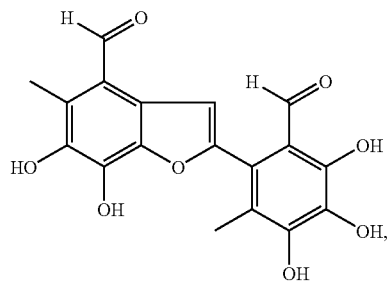

a compound of formula (III)

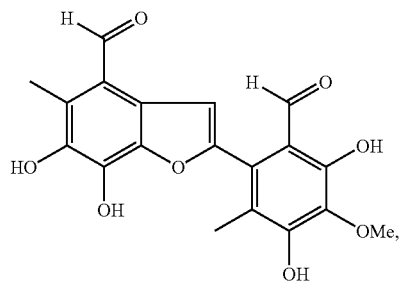

a compound of formula (IV)

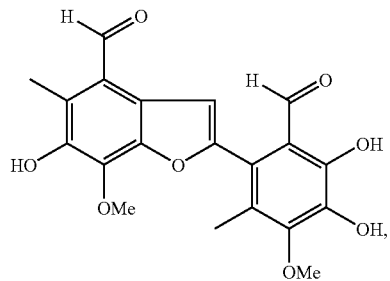

and a compound of formula (V)

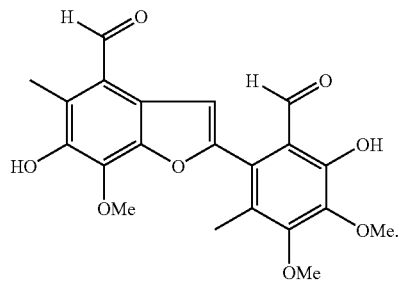

The present invention furthermore relates to all obvious chemical equivalents of the compounds of formula (I) according to the invention. These equivalents are compounds which exhibit a minor chemical difference, and consequently have the same effect, or are converted, under mild conditions, into the compounds according to the invention. Said equivalents also include, for example, salts, reduction products, oxidation products, esters, ethers, acetals or amides of the compounds of the formula (I) as well as equivalents which the skilled person can prepare using standard methods, and, in addition, all optical antipodes and diastereomers, and all stereoisomeric forms.

Physiologically tolerated salts of compounds of the formula (I) are understood as being both their organic salts and their inorganic salts as are described in Remington's Pharmaceutical Sciences (17$^{th}$ Edition, page 1418 (1985)). Because of their physical and chemical stability, and their solubility, sodium salts, potassium salts, calcium salts and ammonium salts are preferred, inter alia, for acid groups; salts of hydrochloric acid, sulfuric acid and phosphoric acid, or of carboxylic acids or sulfonic acids, such as acetic acid, citric acid, benzoic acid, maleic acid, fumaric acid, tartaric acid and p-toluenesulfonic acid, are preferred, inter alia, for basic groups.

DETAILED DESCRIPTION OF THE INVENTION

The compounds of formula (I) according to the invention are unrelated to conventional antibiotics such as the β-lactams (penicillins and cephalosporins), aminoglycosides (streptomycin), macrolides (erythromycin), quinolones (ciprofloxacin), sulfonamides and glycopeptides (vancomycin).

The invention furthermore relates to a process for preparing a compound of formula (I), which comprises 1. fermenting the microorganism Aspergillus flavipes ST003878 (DSM 15290), or one of its variants and/or mutants, in a culture medium until one or more compounds of formula (I) accrues in the culture medium, and
2. isolating a compound of formula (I) from the culture medium, and
3. where appropriate derivatizing the compound of formula (I) and/or converting it into a physiologically tolerated salt.

The invention preferably relates to a process for preparing a compound of formula (I) wherein, in step 1, the compound of formula (II) is formed during the fermentation, in step 2, the compound of formula (II) is isolated and, in step 3, it is derivatized, where appropriate, to give a compound of formula (I) and/or converted into a physiologically tolerated salt.

The process comprises culturing Aspergillus flavipes ST003878 (DSM 15290) under aerobic conditions in a culture medium which contains a carbon source, a nitrogen source, inorganic salts and, where appropriate, trace elements. In this culture medium, Aspergillus flavipes ST003878 (DSM 15290) forms a mixture of compounds of formula (I). The quantitative proportion of one or more of the compounds according to the invention can be varied in dependence on the composition of the culture medium. In addition, the composition of the medium can be used to drive the synthesis of individual compounds.

Suitable carbon sources for the fermentation are assimilable carbohydrates and sugar alcohols, such as glucose, lactose, sucrose, glycerol, starch and D-mannitol, and also carbohydrate-containing natural products, such as malt extract and yeast extract. Examples of nitrogen-containing nutrients are amino acids; peptides and proteins and also their breakdown products, for example, casein, peptones or tryptones; meat extracts; yeast extracts; gluten; ground seeds, for example, from maize, wheat, oats, beans, soybean or the cotton plant; distillation residues from alcohol production; meat meals; yeast extracts; ammonium salts; and nitrates. Preference is given to the nitrogen source being one or more peptides which have been obtained synthetically or biosynthetically. Examples of inorganic salts are chlorides, carbonates, sulfates or phosphates of the alkali metals or alkaline earth metals, iron, zinc, cobalt and manganese. Examples of trace elements are cobalt and manganese.

The culture medium preferably contains glucose, starch, rolled oats and/or glycerol.

The compounds according to the invention are particularly preferably formed in a nutrient solution which contains from about 0.05 to about 5%, preferably from 2 to 3%, of potato starch and from about 0.05 to about 3%, preferably from 0.05 to 1%, of yeast extract. The values in percent are in each case based on the weight of the total nutrient solution.

The microorganism is cultured aerobically, i.e., for example, submerged while being shaken or stirred in shaking flasks or fermenters, or on solid medium, where appropriate, while introducing air or oxygen. The microorganism can be cultured in a temperature range of from about 15 to 35° C., preferably at from about 20 to 30° C., in particular at about 25° C. The pH range should be between 3 and 10, preferably between 4.5 and 6.5. In general, the microorganism is cultured under these conditions over a period of from 2 to 30 days, preferably of from 72 to 360 hours. The organism is advantageously cultured in several steps, i.e. one or more preliminary cultures are initially prepared in a liquid nutrient medium, with these preliminary cultures then being inoculated into the actual production medium, i.e. the main culture, for example, in a volume ratio of 1:10 to 1:100. The preliminary culture is obtained, for example, by inoculating the mycelium into a nutrient solution and allowing it to grow for from about 72 to 360 hours, preferably from 96 to 240 hours. The mycelium can be obtained, for example, by allowing the strain to grow for from about 1 to 20 days, preferably from 6 to 10 days, on a solid or liquid nutrient substrate, for example yeast malt agar, rolled oats agar or potato dextrose agar.

The course of the fermentation, and the formation of the compounds of formula (I) according to the invention, can be monitored in accordance with methods which are known to the skilled person, for example, by means of detecting biological activity in bioassays or by means of chromatographic methods, such as thin layer chromatography (TLC) or high performance liquid chromatography (HPLC).

The fungus Aspergillus flavipes ST003878 (DSM 15290) is able, for example, to form compounds of formula (I) by means of a surface culture or stationary culture on solid nutrient substrates. Solid nutrient substrates are prepared by, for example, adding agar or gelatin to aqueous nutrient media. However, it is also possible to obtain the compound of formula (I) by means of fermenting the fungus Aspergillus flavipes ST003878 (DSM 15290) while submerged, i.e. in an aqueous suspension, with compound (I) usually being located in the culture cell mass. It is, therefore, expedient to separate off the fermentation solution by means of filtration or centrifugation. The filtrate is extracted using an absorption resin as the solid phase. The mycelium and the surface culture are expediently extracted with an organic solvent which is miscible, or partially miscible, with water, for example, a ($C_1$–$C_4$)-alcohol, preferably methanol or 2-propanol.

While the extractions can be carried out over a wide pH range, it is expedient to carry them out in a neutral or weakly acid medium, preferably between pH 3 and pH 7, where appropriate, in the added presence of a reducing agent. The extracts can, for example, be concentrated and dried in vacuo.

One method of purifying the compounds according to the invention is separation between a stationary and a mobile phase, in a manner known per se, for example, by means of chromatography on adsorption resins, for example, on Diaion® HP-20 (Mitsubishi Casei Corp., Tokyo), on Amberlite® XAD 7 (Rohm and Haas, USA) or Amberchrom® CG, (Toso Haas, Philadelphia, USA). Numerous reversed phase supports, for example $RP_8$ and $RP_{18}$, as are well known within the context of high pressure liquid chromatography (HPLC), are also suitable.

Another possibility for purifying the antibiotic according to the invention is that of using what are termed normal-phase chromatography supports, for example, silica gel or $Al_2O_3$, or others, in a manner known per se.

An alternative isolation method is that of using molecular sieves, such as Fractogel® TSK HW-40 (Merck, Germany) or Sephadex® G-25 (Amersham Biosciences), in a manner known per se. In addition to this, it is also possible to use crystallization to isolate biflavipin from enriched material. Organic solvents and their mixtures, either anhydrous or with water added, are, for example, suitable for this purpose. An additional method for isolating and purifying the antibiotics according to the invention consists of using anion exchangers, preferably in a pH range from 4 to 10, and cation exchangers, preferably in a pH range of from 2 to 5. The use of buffer solutions to which portions of organic solvents have been added is particularly suitable for this purpose.

An isolate of the microorganism strain Aspergillus flavipes ST003878 was deposited, in accordance with the rules of the Budapest Treaty, in the Deutsche Sammlung von Mikroorganismen und Zellkulturen [German collection of microorganisms and cell cultures] GmbH (DSMZ), Mascheroder Weg 1B, 38124 Brunswick, Germany, under the number DSM 15290.

The fungus Aspergillus flavipes ST003878 (DSM 15290) has a white substrate mycelium. During sporulation, the color of the mycelium changes to yellow to brown. Cultures on Czapek agar medium which are about 10 days of age form large amounts of yellow to brownish exudates. The conidia are colorless and round, having a diameter of 2–3 µm. The primary and secondary sterigmata are of similar length (5–6 µm) and are brown in color.

Instead of the strain Aspergillus flavipes ST003878 (DSM 15290), it is also possible to use one of its mutants and/or variants which is able to produce one of the compounds of formula (I) according to the invention.

A mutant is a microorganism in which one or more genes in the genome have been modified, with the gene or the genes which is/are responsible, in the case of the present invention, for the ability of the organism to produce one or more of the compounds of formula (I) remaining functional and inheritable.

These mutants can be generated, in a manner known per se, using physical means, for example, irradiation, as with ultraviolet rays or x-rays, or using chemical mutagens, such as ethyl methanesulfonate (EMS); 2-hydroxy-4-methoxy-benzophenone (MOB) or N-methyl-N'-nitro-N-nitrosoguanidine (MNNG), or as described by Brock et al. in "Biology of Microorganisms," Prentice Hall, pages 238–247 (1984).

A variant is a phenotype of the microorganism. Microorganisms have the ability to adapt to their environment and therefore exhibit pronounced physiological flexibility. In the case of phenotypic adaptation, all the cells of the microorganism are involved, with the nature of the change not being genetically conditioned and being reversible under altered circumstances (H. Stolp, Microbial ecology: organism, habitats, activities. Cambridge University Press, Cambridge, GB, page 180, 1988).

Screening for mutants and/or variants which synthesize one or more of the compounds according to the invention is effected in accordance with the following scheme:
lyophilization of the fermentation medium;
extraction of the lyophilizate with an organic solvent:
extraction of a compound from the culture filtrate using solid phases;
analysis by means of HPLC or TLC or by means of testing the biological activity.

The above-described fermentation conditions apply both for Aspergillus flavipes ST003878 (DSM 15290) and for mutants and/or variants thereof.

Derivatizations are carried out as follows: hydroxyl groups of the compound of formula (I) ($R_3$ to $R_7$ are each H) can be esterified using an activated acid, preferably an acid chloride Cl—C(O)—($C_1$–$C_6$)-alkyl ($R_3$ to $R_7$ are, independently of each other, —C(O)—($C_1$–$C_6$)-alkyl). In addition, hydroxyl groups can be etherified by, for example, reaction with a ($C_1$–$C_6$)-alkyl halide in acid medium or by reaction with a trimethylsilyldiazo-($C_1$–$C_6$)-alkyl compound, preferably with trimethylsilyldiazomethane. A phenylic aldehyde function ($R^1$ and/or $R^2$ is H) is, for example, oxidized to an acid function using manganese oxide or using Jones reagent (sulfuric chromium(VI) oxide). The acid function which is formed in this connection can be esterified by means of 4-dimethylaminopyridine (4-DMAP) under Steglich conditions or with a ($C_1$–$C_6$)-alcohol in acid medium. Said derivatizations are examples of methods which are known per se and are described, inter alia, in J. March, Advanced Organic Chemistry, John Wiley & Sons, 4$^{th}$ Edition, 1992. In order to carry out the reactions selectively, it may be advantageous to introduce protecting groups, in a manner known per se, prior to the reaction. The protecting groups are eliminated after the reaction and the reaction product is then purified.

The compounds according to the invention are powerful inhibitors of bacterial N-acetylglucosamine-1-phosphate uridyltransferase (GlmU); they are, therefore, suitable for the treatment and/or prophylaxis of diseases which are caused by bacterial infections or mycoses.

The inhibition of the GlmU can be determined in a biochemical test using the following method:

The assay was carried out in a 384-plate format. The reaction volume was 40 µl per test. The reaction mixture contained 10 µl of test substance and 15 µl of substrate solution consisting of acetylCoA and D-glucosamine-1-phosphate. The enzyme reaction was started by adding 15 µl of GlmU enzyme solution. After 60 minutes of incubation at 30° C., the reaction was stopped by adding 10 µl of developer reagent (DTNB dissolved in guanidine). The plates were then centrifuged (1 min, 1000 rpm) and stored for a further 45 minutes at room temperature before the absorption was read at 405 nm in a photometer. In order to be able to calculate the inhibitory activity of the test compounds, positive controls (signal with GlmU) and negative controls (signal without GlmU) were included on each plate. In order to exclude falsely positive samples, which could be caused by nonspecific substance effects (e.g. color), blank plates, which contained the substances but no GlmU, were included in parallel with the test plates. After correction for the blanks, the inhibitory activities of the substances were calculated in accordance with the following formula:

$$\text{Inhibition}(\%) = 100 \times [1 - (OD_{405\ nm}\ \text{substance}/OD_{405\ nm}\ \text{positive control})]$$

An inhibition constant, $IC_{50}$, of 1 µM was determined for the inhibitory effect of the compound of formula (II) on the enzyme N-acetylglucosamine-1-phosphate uridyltransferase (GlmU).

The invention therefore furthermore relates to the use of a compound of formula (I), preferably of a compound of formula (II), or of a physiologically tolerated salt thereof, for producing a pharmaceutical in human or animal medicine, in particular for producing a pharmaceutical for the treatment and/or prophylaxis of bacterial infectious diseases and/or mycoses.

In addition, the present invention relates to a pharmaceutical having a content of at least one compound of formula (I) according to the invention, preferably having a content of the compound of formula (II).

Said pharmaceutical is produced by mixing at least one compound of formula (I) with one or more pharmacologically suitable auxiliary substances or carrier substances and bringing the mixture into a form suitable for administration.

While the pharmaceuticals according to the invention can be administered orally or parenterally, it is also in principle possible to use them rectally. Examples of suitable solid or liquid galenic preparation forms are granules, powders, tablets, sugar-coated tablets, (micro)capsules, suppositories, syrups, emulsions, suspensions, aerosols, drops or injectable solutions in ampoule form, and also preparations giving a protracted release of active compound, in the production of which use is customarily made of pharmacologically suitable carrier substances or auxiliary substances, such as disintegrants, binders, coating agents, swelling agents, gliders, lubricants, flavorings, sweeteners or solubilizers, for example, magnesium carbonate, titanium dioxide, lactose, mannitol and other sugars, talc, lactalbumin, gelatin, starch, vitamins, cellulose and its derivatives, animal or vegetable oils, polyethylene glycols and solvents, such as water, alcohols, glycerol and polyhydric alcohols.

Where appropriate, the dosage units for oral administration can be microencapsulated in order to delay the release, or extend it over a longer period, as, for example, by means of coating or embedding the active compound, in particle form, in suitable polymers, waxes or the like.

0.1–1000, preferably 0.2–100 mg/kg of body weight is/are administered as an expedient dose. These quantities are expediently administered in dosage units which at least contain the effective daily quantity of the compounds according to the invention, e.g. 30–3000, preferably 50–1000 mg.

The daily dose to be administered depends on the body weight, age, sex and condition of the mammal. However, higher and lower daily doses may sometimes also be appropriate. The daily dose can be administered both by means of a once-only administration in the form of a single dosage unit, or in several smaller dosage units, and by means of the multiple administration of subdivided doses at predetermined intervals.

The following examples are intended to illustrate the invention without limiting the scope of the invention in any way.

Percentage values relate to the weight. Mixing ratios in the case of liquids relate to volume unless otherwise indicated.

EXAMPLE 1

Preparing a Glycerol Culture of Aspergillus flavipes ST003878 (DSM 15290)

30 ml of nutrient solution (malt extract, 2.0%, yeast extract, 0.2%, glucose, 1.0%, $(NH_4)_2HPO_4$, 0.05%, pH 6.0) were inoculated, in a sterile 100 ml Erlenmeyer flask, with the strain Aspergillus flavipes ST003878 (DSM 15290), and incubated for 6 days, at 25° C. and 140 rpm, on a rotating shaker. 1.5 ml of this culture were subsequently diluted with 2.5 ml of 80% glycerol and stored at −135° C.

EXAMPLE 2

Preparing a Preliminary Culture of Aspergillus flavipes ST003878 (DSM 15290) in an Erlenmeyer Flask.

100 ml of nutrient solution (malt extract, 2.0%, yeast extract, 0.2%, glucose, 1.0%, $(NH_4)_2HPO_4$, 0.05%, pH 6.0) are inoculated, in a sterile 300 ml Erlenmeyer flask, with the strain Aspergillus flavipes ST003878 (DSM 15290) and incubated for 4 days, at 25° C. and 140 rpm, on a rotating shaker. 2 ml of this preliminary culture are then inoculated for the purpose of preparing the main cultures.

EXAMPLE 3

Fermenting Aspergillus flavipes ST003878 (DSM 15290) in an Erlenmeyer Flask

In each case, 100 ml of nutrient solution (potato dextrose broth, 2.4%, yeast extract, 0.2%, pH 5.2) are inoculated, in a sterile 300 ml Erlenmeyer flask, with the strain Aspergillus flavipes ST003878 (DSM 15290), and incubated for 11 days, at 25° C. and 140 rpm, on a rotating shaker. 300 ml of this preliminary culture are then inoculated for the purpose of preparing the main cultures.

EXAMPLE 4

Fermenting Aspergillus flavipes ST003878 (DSM 15290) in a Fermenter

A 10 l fermenter is operated under the following conditions:

| | |
|---|---|
| Nutrient medium: | 24 g of potato dextrose broth/l |
| | 2 g of yeast extract/l |
| | pH 5.2 (prior to sterilization) |
| Incubation period: | 166 hours |
| Incubation temperature: | 28° C. |
| Stirrer speed: | 180 rpm |
| Aeration: | 16 L min$^{-1}$ |

Foam formation was suppressed by repeatedly adding an ethanolic solution of polyol. The production maximum was reached after approx. 160 hours.

EXAMPLE 5

Isolating the Compound of the Formula (II)

25 liters of culture solution, obtained as described in example 4, contained 90 mg of the compound of the formula (II). The culture broth was filtered and the mycelium (1.65 kg) was extracted with 10 liters of 2-propanol. The clear alcoholic phase was concentrated down in vacuo to 2 l and, after 1 g of ascorbic acid had been added as antioxidant, loaded onto a column of 785 ml in volume which was filled with the adsorption resin MCI Gel® CHP20P. Column dimensions: width×height: 10 cm×25 cm. The column was eluted with a solvent gradient of from 5% acetonitrile in water to 100% acetonitrile and a column throughput of 15 liters per hour. Fractions which each contained 2.5 liters were collected. Fractions 7 to 9, which contained the compound of formula (II), were checked by HPLC analyses, pooled and concentrated in vacuo. The pH of the solution, which had, to a large extent, been freed from isopropanol, was also adjusted to 4.2 and once again loaded onto an MCI Gel® CHP20P column (490 ml, column dimensions: 5 cm×25 cm). The elution was effected using a gradient of from 0.01% ammonium formate (pH 4.2) to 100% acetonitrile. With the column throughput being 40 ml per minute, fractions containing 200 ml were taken. Fractions 12 and 13 contained the enriched compound of formula (II). They were combined, concentrated in vacuo and, for the purpose of further chromatographic purification, separated on a Luna 10µ C18 phenomenex® column (column dimensions: 21 mm×250 mm). 0.025% trifluoroacetic acid and from 0% to 100% acetonitrile were used as the eluent, with the flow-through rate being 25 ml/minute. The fraction size was 50 ml. Fraction 14 contained the greatly enriched compound of formula (II); it was slightly concentrated in vacuo and left to stand at +4° C. The lemon-yellow compound of formula (II) crystallized out and was filtered off, dried and bottled under argon (20 mg).

EXAMPLE 6

High Pressure Liquid Chromatography (HPLC) of the Compound of Formula (II)

| | |
|---|---|
| Column: | YMC-PRO 18 ®, 120° A, 250–4.4, with precolumn, |
| Mobile phase: | A: 5% acetonitrile in 0.02% trifluoroacetic acid, 2 minutes, |
| | B: 100% acetonitrile, |
| Gradient: | from A to B in 18 minutes. |
| Flow rate: | 1 ml per minute, |

Detection by UV absorption at 210 nm.

The compound of formula (II) was found to have a retention time of 13.9 minutes.

EXAMPLE 7

Characterizing the Compound of Formula (II)

A molar mass (M−H) of 357.0673 was found by means of electron spray ionization mass spectrometry (ESI-MS) in the negative mode while a molecular weight (M+H) of 359.0811 was found in the positive mode, corresponding to the empirical formula $C_{18}H_{14}O_8$ and a molecular weight of 358.31. The physicochemical and spectroscopic properties of compound (II) can be summarized as follows:

Appearance: lemon-yellow crystalline substance which is soluble in medium-polar and polar organic solvents. Stable in neutral and mildly acid medium but unstable in strongly acidic and alkaline solutions and under the influence of oxygen.

Empirical formula: $C_{18}H_{14}O_8$

Molecular weight: 358.31

UV maxima: 220, 245, 307 and 365 nm in water/acetonitrile (1:1) at pH 2.

TABLE 1

Chemical shifts of the compound (II) in DMSO at 300 K.

| | $^1H$ | $^{13}C$ |
|---|---|---|
| 2 | — | 151.57 |
| 3 | 7.47 | 108.94 |
| 3a | — | 122.83 |
| 4 | — | 117.21 |
| 5 | — | 127.54 |
| 5-Me | 2.58 | 11.03 |
| 6 | — | 140.91 |
| 6-OH | broad | — |
| 7 | — | 136.42 |
| 7-OH | broad | — |
| 7a | — | 142.35 |
| 8 | 10.42 | ~190.2 (broad) |
| 9 | — | 124.84 |
| 10 | — | 112.61 |
| 11 | — | 150.17 |
| 11-OH | ~12.1 (broad) | — |
| 12 | — | 132.68 |
| 12-OH | broad | — |
| 13 | — | 151.52 |
| 13-OH | broad | — |
| 14 | — | 118.72 |
| 14-Me | 2.01 | 12.66 |
| 15 | 9.48 | 194.74 |

EXAMPLE 8

Methylating the Compound of Formula (II)

12 mg of the compound of formula (II), obtained as described in example 5, were dissolved in 3 ml of methanol, after which 1 ml of (trimethylsilyl)diazomethane [2 M solution in hexane, Aldrich] was added. The reaction mixture was left to stand at room temperature and the course of the reaction was monitored by HPLC. After the compound of formula (II) employed had been completely reacted, the reaction was terminated by adding water and concentrating in vacuo. The resulting methylation products were purified chromatographically on a Luna 5μ RP18 phenomenex® column using a gradient containing 0.02% trifluoroacetic acid and acetonitrile. After the pure fractions had been freeze-dried, the following were obtained by means of HPLC (conditions as in example 5):

2 mg of compound of formula (III), monomethyl ether, retention time, 15.4 minutes, 2.7 mg of compound of formula (IV), dimethyl ether, retention time, 16.9 minutes, 1.9 mg of compound of formula (V), trimethyl ether, retention time, 19.4 minutes.

EXAMPLE 9

Characterizing the Compound of Formula (III)

In ESI-MS, the compound of formula (III) gave a molecular peak of 373.0 in the positive mode (M+H) and of 371.0 in the negative mode (M−H), corresponding to a MW=372 and an empirical formula of $C_{19}H_{16}O_8$.

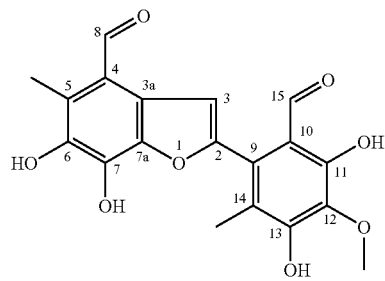

TABLE 2

Chemical shifts of compound (III) in DMSO at 300 K.

| | $^1H$ | $^{13}C$ |
|---|---|---|
| 2 | — | 150.95 |
| 3 | 7.51 | 109.16 |
| 3a | — | 122.65 |
| 4 | — | 117.28 |
| 5 | — | 127.75 |
| 5-Me | 2.58 | 11.06 |
| 6 | — | 141.03 |
| 6-OH | Broad | — |
| 7 | — | 136.47 |
| 7-OH | Broad | — |
| 7a | — | 142.45 |
| 8 | 10.42 | 190.24 |
| 9 | — | 129.11 |
| 10 | — | 112.98 |
| 11 | — | 154.87 |
| 11-OH | 12.22 | — |
| 12 | — | 134.76 |
| 12-OMe | 3.83 | 60.28 |
| 13 | — | 155.68 |
| 13-OH | broad | — |
| 14 | — | 119.05 |
| 14-Me | 2.01 | 12.66 |
| 15 | 9.49 | 194.73 |

EXAMPLE 10

Characterizing the Compound of Formula (IV)

In ESI-MS, the compound of formula (IV) gave a molecular peak of 387.1 in the positive mode (M+H) and of 385.0 in the negative mode, corresponding to a MW=386 and an empirical formula of $C_{20}H_{18}O_8$.

TABLE 3

Chemical shifts of tcompound (IV) in DMSO at 300 K.

| | $^1$H | $^{13}$C |
|---|---|---|
| 2 | — | 151.51 |
| 3 | 7.51 | 108.72 |
| 3a | — | 122.93 |
| 4 | — | 119.83 |
| 5 | — | 127.10 |
| 5-Me | 2.58 | 10.86 |
| 6 | — | 143.62 |
| 6-OH | 9.21 | — |
| 7 | — | 137.18 |
| 7-OMe | 4.15 | 60.44 |
| 7a | — | 143.74 |
| 8 | 10.48 | 190.88 |
| 9 | — | 122.97 |
| 10 | — | 115.84 |
| 11 | — | 150.54 |
| 11-OH | 11.70 | — |
| 12 | — | 139.24 |
| 12-OH | 9.68 | — |
| 13 | — | 151.69 |
| 13-OMe | 3.87 | 59.90 |
| 14 | — | 123.98 |
| 14-Me | 2.08 | 12.80 |
| 15 | 9.72 | 195.45 |

EXAMPLE 11

Characterizing the Compound of Formula (V)

In ESI-MS, the compound of formula (V) gave a molecular peak of 401.1 in the positive mode (M+H) and of 399.0 in the negative mode (M−H), corresponding to MW=400 and an empirical formula of $C_{21}H_{20}O_8$.

TABLE 4

Chemical shifts of compound (V) in DMSO at 300 K.

| | $^1$H | $^{13}$C |
|---|---|---|
| 2 | — | 150.90 |
| 3 | 7.56 | 108.95 |
| 3a | — | 122.73 |
| 4 | — | 119.91 |
| 5 | — | 127.28 |
| 5-Me | 2.58 | 10.85 |
| 6 | — | 143.74 |
| 6-OH | 9.25 | — |
| 7 | — | 137.18 |
| 7-OMe | 4.14 | 60.45 |
| 7a | — | 143.82 |
| 8 | 10.48 | 190.88 |
| 9 | — | 127.83 |
| 10 | — | 116.20 |
| 11 | — | 155.63 |
| 11-OH | 11.82 | — |
| 12 | — | 140.70 |
| 12-OMe | 3.88 | 60.53 |
| 13 | — | 156.89 |
| 13-OMe | 3.98 | 60.74 |
| 14 | — | 123.77 |

TABLE 4-continued

Chemical shifts of compound (V) in DMSO at 300 K.

| | $^1$H | $^{13}$C |
|---|---|---|
| 14-Me | 2.06 | 12.85 |
| 15 | 9.73 | 195.00 |

What is claimed is:

1. A compound of formula (I)

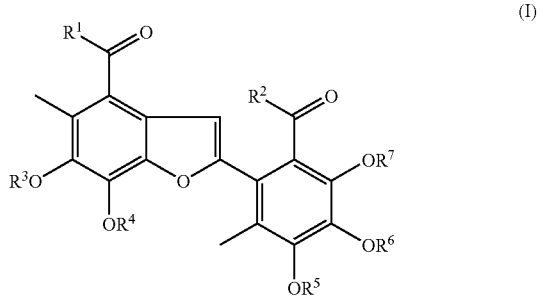

(I)

wherein
R$^1$ and R$^2$ are, independently of each other, H, OH or —O—(C$_1$–C$_6$)-alkyl, and
R$^3$, R$^4$, R$^5$, R$^6$ and R$^7$ are, independently of each other, H, —(C$_1$–C$_6$)-alkyl or —C(O)—(C$_1$–C$_6$)-alkyl,
or a physiologically tolerated salt of a compound of formula (I).

2. A compound of formula (I) as claimed in claim 1, wherein both R$^1$ and R$^2$ are H.

3. A compound of formula (I) as claimed in claim 1, wherein R$^3$, R$^4$, R$^5$, R$^6$ and R$^7$ are, independently of each other, H or methyl.

4. A compound of formula (I) as claimed in claim 1, which is the compound of formula (II):

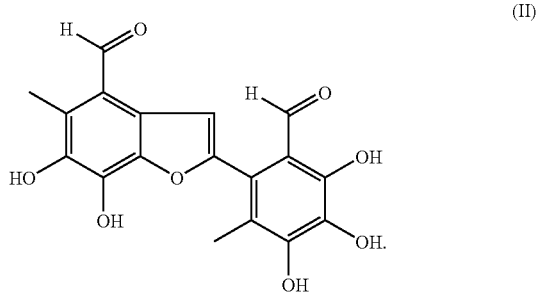

(II)

5. A compound of formula (I) as claimed in claim 1, which has the formula (III):

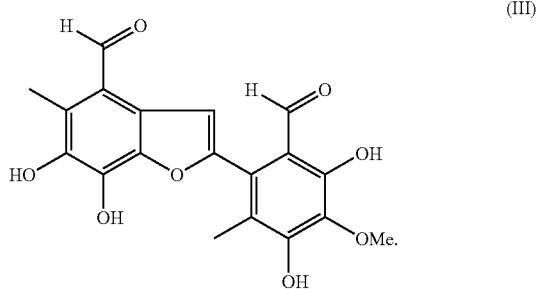

(III)

6. A compound of formula (I) as claimed in claim 1, which is the compound of formula (IV):

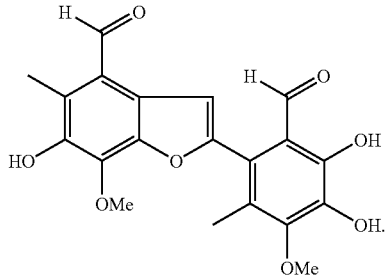

(IV)

7. A compound of formula (I) as claimed in claim 1, which is characterized by formula (V):

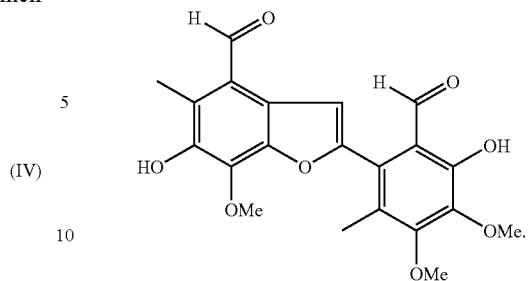

(V)

8. A pharmaceutical composition comprising a compound of formula (I) as claimed in claim 1, or of a physiologically tolerated salt thereof.

9. The pharmaceutical composition of claim 8 for the treatment and/or prophylaxis of bacterial infectious diseases and/or mycoses.

10. A process for producing a pharmaceutical as claimed in claim 9, which comprises mixing at least one compound of formula (I) with one or more pharmacologically suitable auxiliary substances or carrier substances.

* * * * *